(12) United States Patent
Tsern et al.

(10) Patent No.: US 12,029,324 B2
(45) Date of Patent: Jul. 9, 2024

(54) ADAPTIVE SLEEP SYSTEM USING DATA ANALYTICS AND LEARNING TECHNIQUES TO IMPROVE INDIVIDUAL SLEEP CONDITIONS

(71) Applicant: Bryte, Inc., Los Altos, CA (US)

(72) Inventors: Ely Tsern, Los Altos, CA (US); Jonathan Farringdon, Pittsburgh, PA (US); John Tompane, Los Altos, CA (US); Richard Tompane, San Diego, CA (US); William Burnett, San Francisco, CA (US)

(73) Assignee: Bryte, Inc., Los Altos, CA (US)

( * ) Notice: Subject to any disclaimer, the term of this patent is extended or adjusted under 35 U.S.C. 154(b) by 0 days.

(21) Appl. No.: 17/808,503

(22) Filed: Jun. 23, 2022

(65) Prior Publication Data
US 2023/0143759 A1    May 11, 2023

Related U.S. Application Data

(63) Continuation of application No. 16/783,054, filed on Feb. 5, 2020, now Pat. No. 11,369,207, which is a
(Continued)

(51) Int. Cl.
*G05D 16/20* (2006.01)
*A47C 21/04* (2006.01)
(Continued)

(52) U.S. Cl.
CPC ............ *A47C 27/083* (2013.01); *A47C 21/04* (2013.01); *A47C 27/082* (2013.01);
(Continued)

(58) Field of Classification Search
CPC .................................................. G05D 16/2066
See application file for complete search history.

(56) References Cited

U.S. PATENT DOCUMENTS

| | | |
|---|---|---|
| 3,656,190 A | 4/1972 | Regan et al. |
| 4,222,137 A | 9/1980 | Usami |

(Continued)

FOREIGN PATENT DOCUMENTS

| | | |
|---|---|---|
| KR | 10-2016-0030737 A | 3/2016 |
| KR | 10-2016-0055642 A | 5/2016 |
| KR | 10-2017-0065853 A | 6/2017 |

OTHER PUBLICATIONS

International Search Report on PCT Application No. PCT/US2017/044764 from International Searching Authority (KIPO) dated Nov. 30, 2017.
(Continued)

*Primary Examiner* — Suresh Suryawanshi
(74) *Attorney, Agent, or Firm* — KPPB LLP

(57) ABSTRACT

A bed integrates sensors and other inputs to detect specific sleep environment conditions including point-specific pressure and/or temperature conditions. The bed includes a controller for commanding actuator or other devices to adjust these conditions. The controller may do so based on reference patterns for conditions and profiles of desired conditions. Information regarding the conditions may be provided to a remote computer, which may analyze the conditions and provide revised profiles of desired conditions.

18 Claims, 9 Drawing Sheets

Related U.S. Application Data continuation of application No. 15/665,358, filed on Jul. 31, 2017, now Pat. No. 10,561,253.

(60) Provisional application No. 62/368,773, filed on Jul. 29, 2016.

(51) Int. Cl.

| | |
|---|---|
| *A47C 27/08* | (2006.01) |
| *A61B 5/00* | (2006.01) |
| *A61M 21/02* | (2006.01) |
| *G05B 13/02* | (2006.01) |
| *A47C 27/14* | (2006.01) |
| *A61B 5/0295* | (2006.01) |
| *A61B 5/11* | (2006.01) |
| *A61B 5/113* | (2006.01) |
| *A61B 5/25* | (2021.01) |
| *A61M 21/00* | (2006.01) |

(52) U.S. Cl.
CPC .......... *A61B 5/0036* (2018.08); *A61B 5/4815* (2013.01); *A61B 5/6892* (2013.01); *A61B 5/7267* (2013.01); *A61M 21/02* (2013.01); *G05B 13/024* (2013.01); *G05B 13/0265* (2013.01); *A47C 27/14* (2013.01); *A61B 5/0295* (2013.01); *A61B 5/1102* (2013.01); *A61B 5/1118* (2013.01); *A61B 5/113* (2013.01); *A61B 5/25* (2021.01); *A61B 5/4812* (2013.01); *A61B 5/7275* (2013.01); *A61B 5/7282* (2013.01); *A61B 5/746* (2013.01); *A61B 2562/0204* (2013.01); *A61B 2562/0219* (2013.01); *A61B 2562/0247* (2013.01); *A61B 2562/0271* (2013.01); *A61M 2021/0016* (2013.01); *A61M 2021/0022* (2013.01); *A61M 2021/0027* (2013.01); *A61M 2021/0044* (2013.01); *A61M 2021/0066* (2013.01); *A61M 2205/3553* (2013.01); *A61M 2205/3561* (2013.01); *A61M 2230/005* (2013.01); *A61M 2230/04* (2013.01); *A61M 2230/30* (2013.01); *A61M 2230/42* (2013.01); *A61M 2230/50* (2013.01); *A61M 2230/63* (2013.01)

(56) References Cited

U.S. PATENT DOCUMENTS

| | | | |
|---|---|---|---|
| 5,283,735 A * | 2/1994 | Gross .................... | B60N 2/914 5/616 |
| 5,625,914 A | 5/1997 | Schwab | |
| 5,980,755 A | 11/1999 | Roberts et al. | |
| 7,524,279 B2 | 4/2009 | Auphan | |
| 7,676,872 B2 | 3/2010 | Block et al. | |
| 7,941,882 B1 | 5/2011 | Strozer | |
| 7,967,739 B2 | 6/2011 | Auphan | |
| 8,161,826 B1 | 4/2012 | Taylor | |
| 8,533,879 B1 | 9/2013 | Taylor | |
| 8,661,915 B2 | 3/2014 | Taylor | |
| 8,690,751 B2 | 4/2014 | Auphan | |
| 8,752,222 B2 * | 6/2014 | Papaioannou ......... | G05B 15/02 5/722 |
| 8,800,386 B2 | 8/2014 | Taylor | |
| 8,813,285 B2 | 8/2014 | Oexman et al. | |
| 9,642,470 B2 | 5/2017 | Taylor | |
| 9,833,188 B2 | 12/2017 | Oakhill | |
| 9,933,775 B2 | 4/2018 | Saavedra | |
| 9,955,791 B2 | 5/2018 | Chandler et al. | |
| 10,744,390 B1 | 8/2020 | Kahn et al. | |
| 10,945,659 B1 | 3/2021 | Kahn et al. | |
| 2006/0183980 A1 | 8/2006 | Yang | |
| 2007/0094806 A1 | 5/2007 | Beretta | |
| 2008/0209641 A1 * | 9/2008 | Boyd ....................... | A47G 9/10 5/706 |
| 2010/0302044 A1 | 12/2010 | Chacon et al. | |
| 2011/0010014 A1 | 1/2011 | Oexman et al. | |
| 2013/0283530 A1 | 10/2013 | Main et al. | |
| 2015/0170058 A1 | 6/2015 | Fu | |
| 2015/0208814 A1 | 7/2015 | Alletto, Jr. et al. | |
| 2015/0351982 A1 | 12/2015 | Krenik | |
| 2016/0015184 A1 | 1/2016 | Nunn et al. | |
| 2016/0100696 A1 | 4/2016 | Palashewski et al. | |
| 2016/0106361 A1 | 4/2016 | Miles et al. | |
| 2016/0151603 A1 | 6/2016 | Shouldice et al. | |
| 2017/0202366 A1 * | 7/2017 | Mackey ................. | A47C 27/10 |
| 2017/0224124 A1 * | 8/2017 | Blumberg .............. | A47C 17/34 |
| 2018/0078197 A1 | 3/2018 | Ware et al. | |
| 2019/0069838 A1 | 3/2019 | Xin et al. | |
| 2020/0077942 A1 | 3/2020 | Youngblood et al. | |

OTHER PUBLICATIONS

Written Opinion on PCT Application No. PCT/US2017/044764 from International Searching Authority (KIPO) dated Nov. 30, 2017.

International Search Report on PCT Application No. PCT/US2019/030291 from International Searching Authority (KIPO) dated Aug. 7, 2019.

Written Opinion on PCT Application No. PCT/US2019/030291 from International Searching Authority (KIPO) dated Aug. 7, 2019.

International Search Report on PCT Application No. PCT/US2019/030281 from International Searching Authority (KIPO) dated Aug. 7, 2019.

Written Opinion on PCT Application No. PCT/US2019/030281 from International Searching Authority (KIPO) dated Aug. 7, 2019.

Communication from the European Patent Office (EPO) on European Patent Application No. 17835435.3 dated Dec. 3, 2019.

Extended European Search Report (EESR) from the European Patent Office (EPO) on European Patent Application No. 17835435.3 dated Mar. 25, 2020.

U.S. Appl. No. 15/665,358, filed Jul. 31, 2017, Ely Tsern Jonathan Farringdon John Tompane Richard Tompane William Burnett, US 2018-0125256 A1, Office Action Dec. 10, 2018 Notice of Allowance Jul. 17, 2019 Nov. 21, 2019.

U.S. Appl. No. 16/783,054, filed Feb. 5, 2020, Ely Tsern Jonathan Farringdon John Tompane Richard Tompane William Burnett, US 2020-0315368 A1, Office Action May 18, 2021 Notice of Allowance Jan. 20, 2022 May 17, 2022.

* cited by examiner

ADAPTIVE SLEEP SYSTEM USING DATA ANALYTICS AND LEARNING TECHNIQUES TO IMPROVE INDIVIDUAL SLEEP CONDITIONS

CROSS REFERENCE TO RELATED APPLICATIONS

This application is a continuation U.S. patent application Ser. No. 16/783,054, filed Feb. 5, 2020; which is a continuation of U.S. patent application Ser. No. 15/665,358, filed Jul. 31, 2017, which claims the benefit of the filing date of U.S. Provisional Patent Application No. 62/368,773, filed on Jul. 29, 2016, the disclosures of which are incorporated by reference herein.

BACKGROUND OF THE INVENTION

The present invention relates to sleep, the environmental and physiological elements that might affect sleep, and the potential for improving the sleep experience of an individual.

It is well known that there are numerous factors that can affect sleep; and a lack of sleep or poor quality sleep can have a negative influence on people's health, wellness, and productivity.

The quality of sleep generally depends on the length and depth of the distinct sleep stages (or sleep phases). According to the American Academy of Sleep Medicine (AASM), there are four stages of sleep: REM (Rapid Eye Movement), and three non-REM sleep stages (NREM: N1, N2, and N3), where N3 is also called delta sleep or slow-wave sleep. N1 is the lightest sleep and N1 can sometimes be considered awake, adults spend the majority of the night in N2, and N3 and REM are deeper sleep. Sleep quality and other functions of sleep such as feeling refreshed and memory consolidations are linked to the length and depth of sleep in REM and deep sleep stages. Different sleep environments and conditions can directly affect sleep quality, including sleep position, neck and spinal alignment, higher pressure points on muscles and joints, and temperature hot or cold spots. Furthermore, breathing problems, such as snoring and apnea, in which breathing is constrained or blocked causing regular arousals, commonly interrupt sleep and prevent achieving or staying in deeper sleep stages. To help improve apnea and snoring, it is well known that sleeping in the side position (vs. supine (back) or front) significantly improves breathing passageways, and in fact, resolves the apnea condition for over 50% of the apnea cases. However, as people age, it becomes more difficult to sleep comfortably in the side position, so for comfort reasons, many people must sleep on their backs, which then exacerbates breathing problems.

Because each individual has a different body type, shape, and condition, as well as different lifestyles, health conditions, and needs, the ideal sleep environment for each individual may be custom and personalized. Furthermore, sleep activity itself is a dynamic activity, with changing positions, sleep stages, temperature changes, environmental changes (light, sounds), as well as influence of sleeping partner. Static sleep solutions (beds, cushions, pillows) that are widely used today have fixed characteristics and don't change characteristics throughout the sleep cycle. Furthermore, data on how effective changes in environment and sleep condition improve quality of sleep is today generally limited to imperfect sleep studies, often performed in artificial environments.

BRIEF SUMMARY OF INVENTION

Recent advances in computation power has enabled scaled use of artificial intelligence, learning algorithms and methods, and data analytics. These methods include machine learning, pattern matching, deep learning, and data analysis, which can be used not only to analyze patterns and correlations using large data sets, but also lead to learned iterative improvements in closed-loop robotic systems, where control algorithms that control electro-mechanical systems enabled with various sensors can be improved over time through sensor data analysis and measured trials and experimentation. An example of such systems are self-driving technologies in automobiles. A sleep system that provides a complete closed-loop system coupling both sensor data and an adaptable, controllable bed environment would enable the use of these analytics and learning techniques to make significant improvements in sleep quality for individuals and larger populations.

The invention includes methods and systems, devices, and/or combination of apparatuses to provide a reactive and/or adaptive sleep system and methods for using individual and collective group analytics and learning techniques to improve sleep quality. Some embodiments in accordance with aspects of the invention comprise a bed system and analytics platform with multiple elements, which may include one, some, or all of:

1) a bed system that integrates
   a) sensors and other inputs to detect specific sleep environment conditions (including point-specific pressure and support, temperature, sound and/or light), physiological conditions and position, and other user and environmental context,
   b) specific array of actuators or other devices that can be controlled to physically enable a dynamic sleep surface and/or environment for an individual or multiple individuals in a multi-zone configuration and
   c) a modular physical design to ease shipment, portability, user-assembly and/or inventory logistics,
   d) a controller, including at least one processor, configured to command actuation of the actuators, collect and/or process sensor data, and communicate over a network to a remote computer that performs data analytic and learning algorithms and methods,
2) methods to
   a) analyze user conditions and context
   b) generate control signals to adjust and optimize dynamically the sleep surface and/or environment in order to maximize sleep quality based on metrics
   c) learn which combination control signals and sequences result in improved sleep quality for the user and collection of users, and
3) a network-connected data analytics and learning architecture that performs methods to analyze user and platform data across user groups in order to optimize sleep control configurations for individual users, for example to measure effectiveness and learn iterative optimizations and improvements for individuals and different subgroups who share common characteristics.

Embodiments of this architecture may support the combination of data collection, methods of analysis and learning, and control feedback instructions (both locally and across larger groups), which in some embodiments can be used to dynamically adjust fine resolution physical controls of this sleep environment that enable sleep quality improvements customized to a specific sleeper and their current sleep and environmental states.

In some embodiments a bed system includes a sleeping surface, electrical and/or electromechanical components to adjust position and/or temperature of the sleeping surface on a localized basis, sensors to sense at least one physical parameter associated with the sleeping surface, sensors to sense the user's health vitals or statistics, and a controller to command operation of the electrical and/or electromechanical components based on information from the sensors. In some embodiments the controller commands operation of the electrical and/or electromechanical components based on information from the sensors and information relating to a therapy profile for a user of the bed system. In some embodiments the controller provides information relating to the electrical and/or electromechanical components and the information from the sensors to a server, and uses information from the server in commanding operation of the electrical and/or electromechanical components.

In some embodiments, a bed system comprises a sleeping surface, at least one array of actuators to adjust position of the sleeping surface, at least one array of sensors to provide an indication of a physical parameter associated with the sleep surface, and a controller configured to command actuation of the actuators based on the indication of the physical parameter. In some embodiments the physical parameter is pressure. In some embodiments the physical parameter is temperature. In some embodiments the array of actuators is an array of modules including a plurality of actuators. In some embodiments the controller is configured to commonly control all of the plurality of actuators of a particular module. In some embodiments the sensors of the at least one array of sensors is commonly mounted with the actuators of the at least one array of actuators. In some embodiments the bed system further comprises at least one additional array of sensors to provide an indication of an additional physical parameter associated with the sleep surface. In some such embodiments the physical parameter is temperature and the additional physical parameter is pressure. In some embodiments the controller is additionally configured to command actuation of the actuators based on information received from a server.

In some embodiments, a method, performed by at least one processor, for assisting in adjusting a sleep platform environment with localized pressure and temperature control regions across the sleep surface, comprises: receiving information from a plurality of sleep platforms, the information including localized pressure and temperature information over time for a plurality of locations across each of the sleep platforms; receiving information relating to a corresponding plurality of users of the plurality of sleep platforms, the information including heart and/or respiratory information or other health vitals and statistics over time; determining a therapy profile including updated localized pressure and temperature control information for at least one user sleep platform based on the received information from the plurality of sleep platforms and users; and sending the therapy profile to at least one user sleep platform to update the control settings of the sleep platform.

Some embodiments in accordance with aspects of the invention provide a bed system, comprising: a sleep surface; a plurality of sensors for providing indications of pressure for a first plurality of different locations of the sleep surface; a plurality of actuators to adjust pressures for a second plurality of different locations of the sleep surface; and a controller configured to receive the indications of pressure and to command the plurality of actuators to adjust the pressures based the indications of pressures and a relationships between indications of pressure and desired pressures.

Some embodiments in accordance with aspects of the invention provide a method for adjusting a sleep surface of a bed, comprising: measuring indications of pressure for a plurality of locations of the sleep surface; comparing the indications of pressure to at least one reference data pattern for indications of pressure for the plurality of locations of the sleep surface; commanding adjustment of pressure for portions of the sleep surface based on results of the comparison.

Some embodiments in accordance with aspects of the invention provide a method, performed by at least one processor, for assisting in adjusting a sleep platform environment with localized pressure regions across the sleep surface, comprising: receiving information from a plurality of sleep platforms, the information including localized pressure over time for a plurality of locations across each of the sleep platforms; receiving information relating to a corresponding plurality of users of the plurality of sleep platforms, the information including heart and/or respiratory information over time; determining updated localized pressure control information for at least one user sleep platform based on the received information from the plurality of sleep platforms and users; and sending the updated localized pressure control information to at least one user sleep platform to update the control settings of the sleep platform.

Some embodiments in accordance with aspects of the invention provide a bed system, comprising: a sleep surface; a plurality of sensors for providing indications of temperature for a first plurality of different locations of the sleep surface; a plurality of temperature control apparatuses to adjust temperature for a second plurality of different locations of the sleep surface; and a controller configured to receive the indications of temperature and to command the plurality of temperature control apparatuses to adjust the temperatures based the indications of temperature and a relationships between indications of temperature and desired temperatures.

Some embodiments in accordance with aspects of the invention provide a method for adjusting a sleep surface of a bed, comprising: measuring indications of temperature for a plurality of locations of the sleep surface; comparing the indications of temperature to at least one reference data pattern for indications of temperature for the plurality of locations of the sleep surface; commanding adjustment of temperature for portions of the sleep surface based on results of the comparison.

Some embodiments in accordance with aspects of the invention provide a method, performed by at least one processor, for assisting in adjusting a user sleep platform environment with localized pressure regions across the sleep surface, comprising: measuring indications of pressure over time for a plurality of locations of the sleep surface; comparing the indications of pressure to at least one reference data pattern for indications of pressure for the plurality of locations of the sleep surface; commanding localized pressure control information for adjusting for portions of the sleep surface based on results of the comparison; measuring the sleep quality of the user using the sleep platform environment; comparing information from the user sleep platform with a plurality of different sleep platforms, the information including the measured sleep quality of the users for each of the sleep platforms; selecting the pressure control information among the sleep platforms based on the best sleep quality measurement; updating the control settings of the user sleep platform based on the selected pressure control information.

Some embodiments in accordance with aspects of the invention provide a method, performed by at least one processor, for assisting in adjusting a user sleep platform environment with localized pressure regions across the sleep surface, comprising: measuring indications of pressure for a plurality of locations of the sleep surface for a given time period; comparing the indications of pressure to at least one reference data pattern for indications of pressure for the plurality of locations of the sleep surface; commanding localized pressure control information for adjusting for portions of the sleep surface based on results of the comparison for that given time period; measuring the sleep quality of the user using the sleep platform environment for that given time period; comparing information from that time period with the information of the same user sleep platform environment from different time periods, the information including the measured sleep quality of the user for each of the different time periods; selecting the pressure control information among the time periods based on the best sleep quality measurement; updating the control settings of the user sleep platform based on the selected pressure control information.

Some embodiments in accordance with aspects of the invention provide a method, performed by at least one processor, for assisting in adjusting a user sleep platform environment with localized temperature regions across the sleep surface, comprising: measuring indications of temperature over time of the sleep surface; comparing the indications of temperature to at least one reference data pattern for indications of temperature of the sleep surface; commanding temperature control information for adjusting the sleep surface temperature based on results of the comparison; measuring the sleep quality of the user using the sleep platform environment; comparing information from the sleep platform with a plurality of different sleep platforms, the information including the measured sleep quality of the users for each of the sleep platforms; selecting the temperature control information among the sleep platforms based on the best sleep quality measurement; updating the control settings of the user sleep platform based on the selected temperature control information.

Some embodiments in accordance with aspects of the invention provide a method, performed by at least one processor, for assisting in adjusting a user sleep platform environment with localized temperature regions across the sleep surface, comprising: measuring indications of temperature of the sleep surface for a given time period; comparing the indications of temperature to at least one reference data pattern for indications of temperature of the sleep surface; commanding temperature control information for adjusting for the sleep surface based on results of the comparison for that given time period; measuring the sleep quality of the user using the sleep platform environment for that given time period; comparing information from that time period with the information of the same user sleep platform environment from different time periods, the information including the measured sleep quality of the user for each of the different time periods; selecting the temperature control information among the time periods based on the best sleep quality measurement; updating the control settings of the user sleep platform based on the selected temperature control information.

These and other aspects of the invention are more fully comprehended upon review of this disclosure.

DETAILED DESCRIPTION

The invention includes methods and systems, devices, and/or combination of apparatuses to provide a reactive and/or adaptive sleep system and methods for using individual and collective group analytics and learning techniques to improve sleep quality. Some embodiments in accordance with aspects of the invention comprise a bed system and analytics and learning platform with multiple elements, which may include one, some, or all of:

1) a bed system that integrates
  a) sensors and other inputs to detect specific sleep environment conditions (including point-specific pressure and support, temperature, sound and/or light), physiological conditions and position, and other user and environmental context,
  b) specific array of actuators or other devices that can be controlled to physically enable a dynamic sleep surface and/or environment for an individual or multiple individuals in a multi-zone configuration,
  c) a modular physical design to ease shipment, portability, user-assembly and/or inventory logistics,
  d) a controller, including at least one processor, configured to command actuation of the actuators, collect and/or process sensor data, and communicate over a network to a remote computer that performs data analytic and learning algorithms and methods,
2) methods to
  a) analyze user conditions and context
  b) generate control signals to adjust and optimize dynamically the sleep surface and/or environment in order to maximize sleep quality based on metrics c) learn which combination control signals and sequences result in improved sleep quality for the user and collection of users, and 3) a network-connected data analytics and learning architecture that performs methods to analyze user and platform data across user groups in order to optimize sleep control configurations for individual users, for example to measure effectiveness and learn iterative optimizations and improvements for individuals and different subgroups who share common characteristics.

Figure 1:
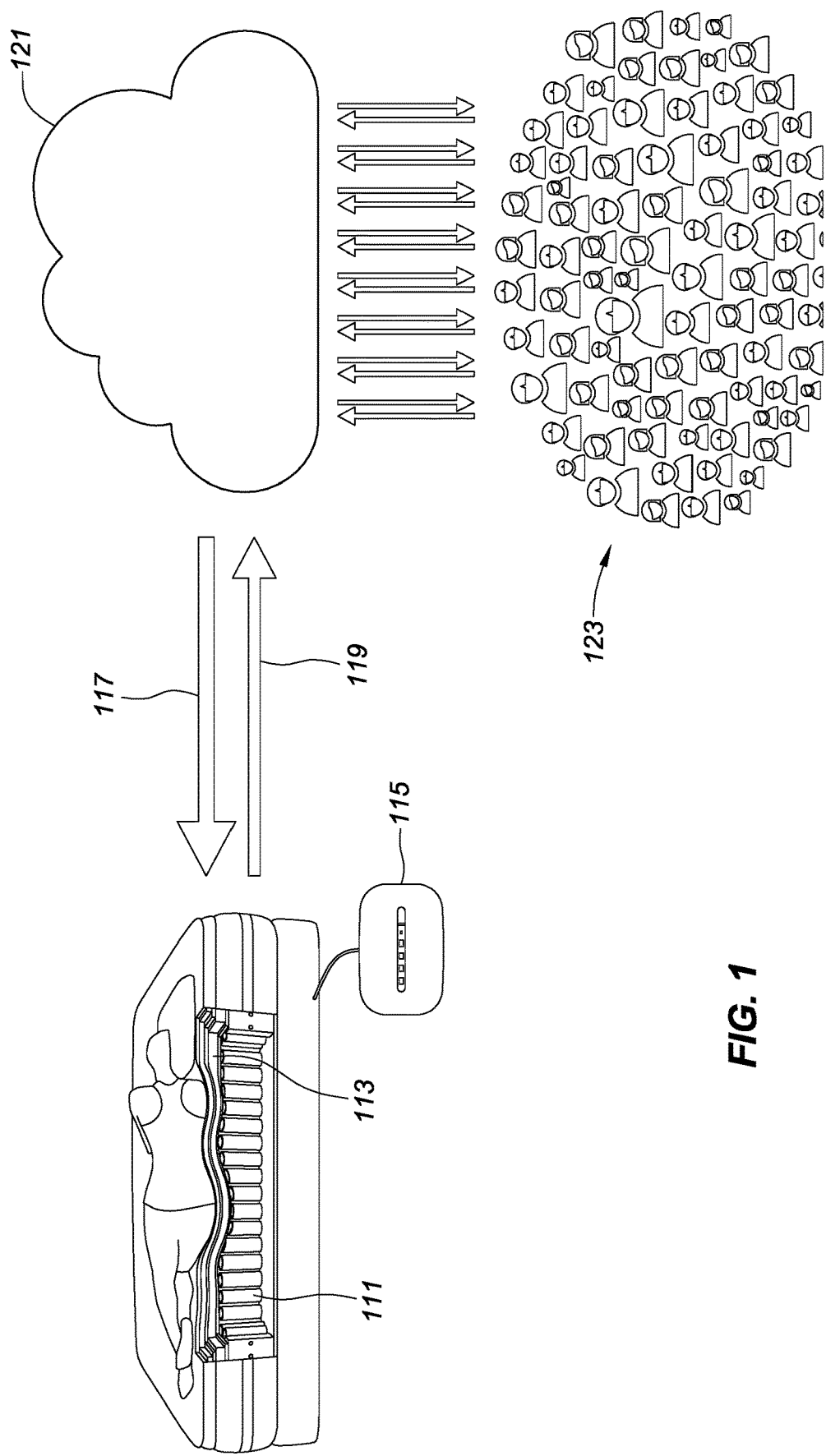
FIG. 1 shows an embodiment of a dynamic bed system and associated information in accordance with aspects of the invention.

FIG. 1 shows a high level description of the entire system showing a bed system with integrated sensors and dynamic, location-specific support and temperature control of the sleep surface, controlled by a local controller 115 which manages the sleep environment and communicates with one or more remote cloud servers 121 that run a sleep therapy analytics and learning program that analyzes user and platform data across multiple users 123 to determine optimal control parameters, heuristics and settings (named Therapy Profile) for the individual user, which are sent back 117 and updated to the user's bed system. The bed system may include a bed with temperature and sensor layers 113 and adjustable coils 111.

This disclosure details aspects of various embodiments in the following sections for a physical architecture and for analysis and control methods, including methods to analyze conditions and context and dynamically adjust sleep conditions in real-time, and methods for multiuser analysis and sleep configuration and control optimizations.

Physical Architecture

Some embodiments provide fine-resolution dynamic surface control, which provides control, precise control of one, some, or all firmness, displacement, and temperature of individual zones across a sleeping surface. In some embodiments dynamic surface control is enabled with a combination of an array of "digital coils", which provide for digital control of the relative firmness level and displacement across the surface, integrated zonal temperature control for local heating and cooling, and the integration of a combination of sensors to determine localized pressure, displacement, movement, and temperature across the surface. In some embodiments, methods to evaluate, analyze and use sensor and context information to determine exact control instructions and configuration changes that are used to control the digital coils and temperature zone mechanisms to improve sleep conditions in real-time are utilized.

Figure 3:
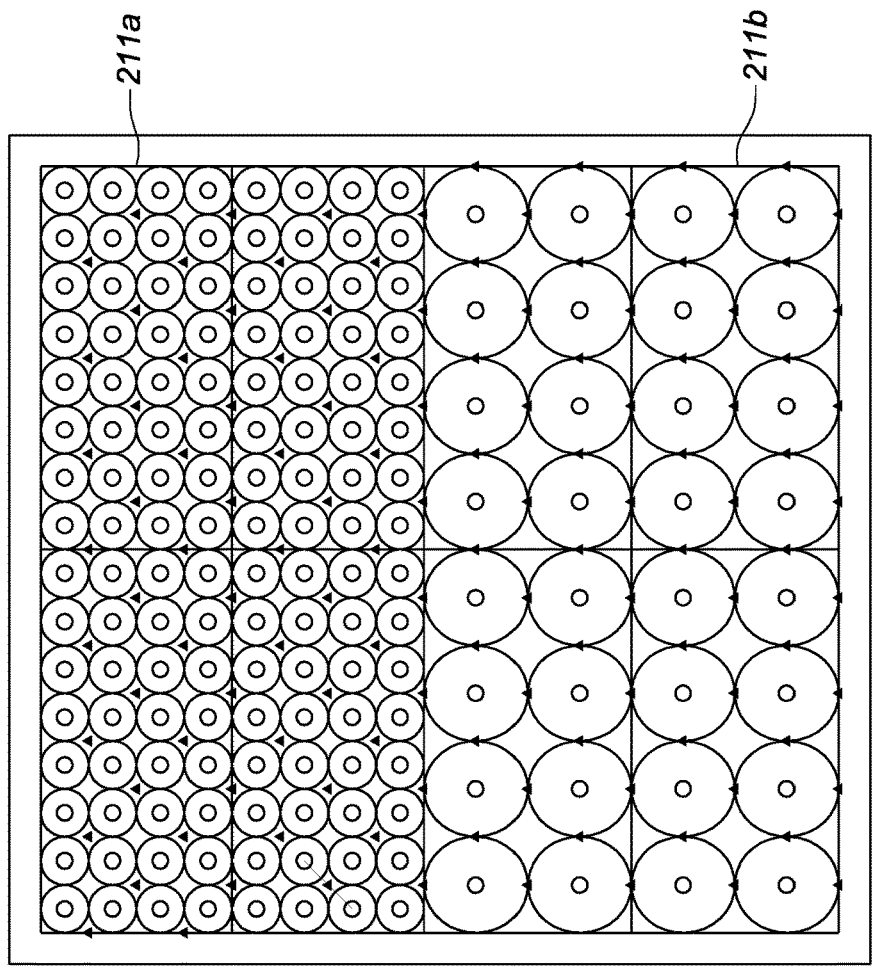
FIG. 3 shows a top view of an embodiment of a bed with sensor and digital coil module arrays in accordance with aspects of the invention.
Figure 2:
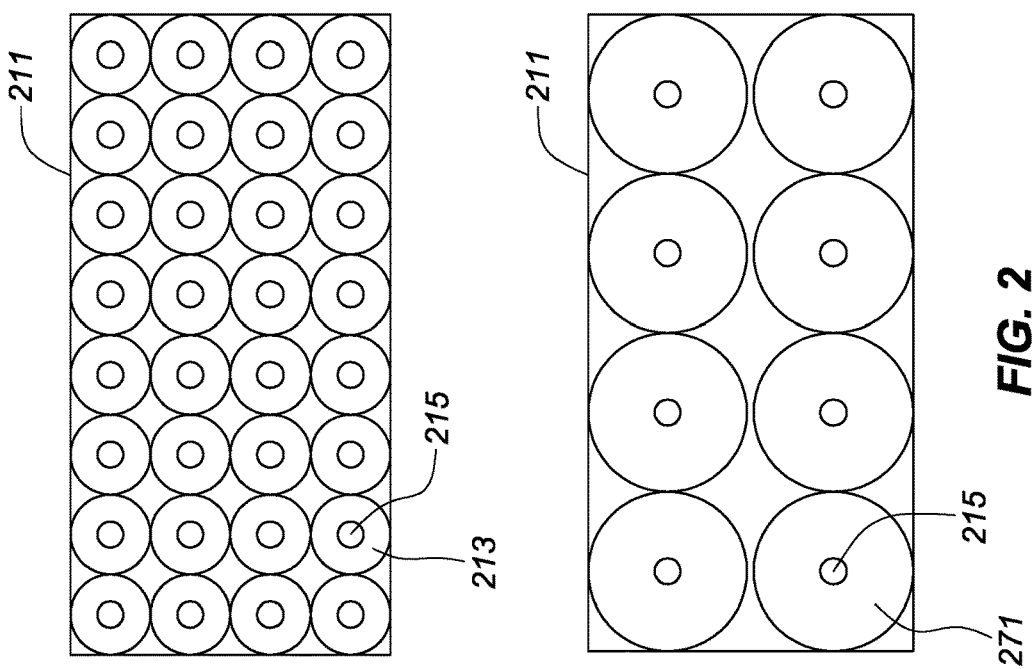
FIG. 2 shows top views of two embodiments of a digital coil module in accordance with aspects of the invention.

The control of the support and firmness of small, localized zones of the surface may be performed by a "digital coil", which is a mechanism below the upper sleep surface that controls firmness level and displacement of a localized area of the bed surface. Digital coils 213, 271 may be distributed in an array below the upper sleep surface, as illustrated in FIGS. 2 and 3.

Top surface area: The digital coil can be of different top surface area sizes, and shapes in some embodiments. The surface area size is set to provide adequate spatial resolution to effectively relieve or support specific body parts on the bed. For instance, around the head, neck and shoulder areas, which may be more sensitive to pressure points and alignment, smaller coil sizes, such as <5 cm in diameter, can be used to provide enough control and spatial resolution to provide adequate dynamic support relief and adjustments. Alternatively, in the areas around the legs and feet, larger coils, such as <15 cm in diameter, can be used to provide dynamic support relief and adjustments given the larger size of the lower body parts and different weights of the limbs.

Shape: The digital coil can also have different volumetric shapes. Different digital coil mechanisms are used in various embodiments, and depending on the mechanism and cost or manufacturing constraints, different volumetric shapes can be used, such as cylinder, rectangle, cube, cones, or hexagonal prisms.

To provide the Digital Coil functionality of controlled firmness and displacement support, different embodiments are possible.

Figure 9:
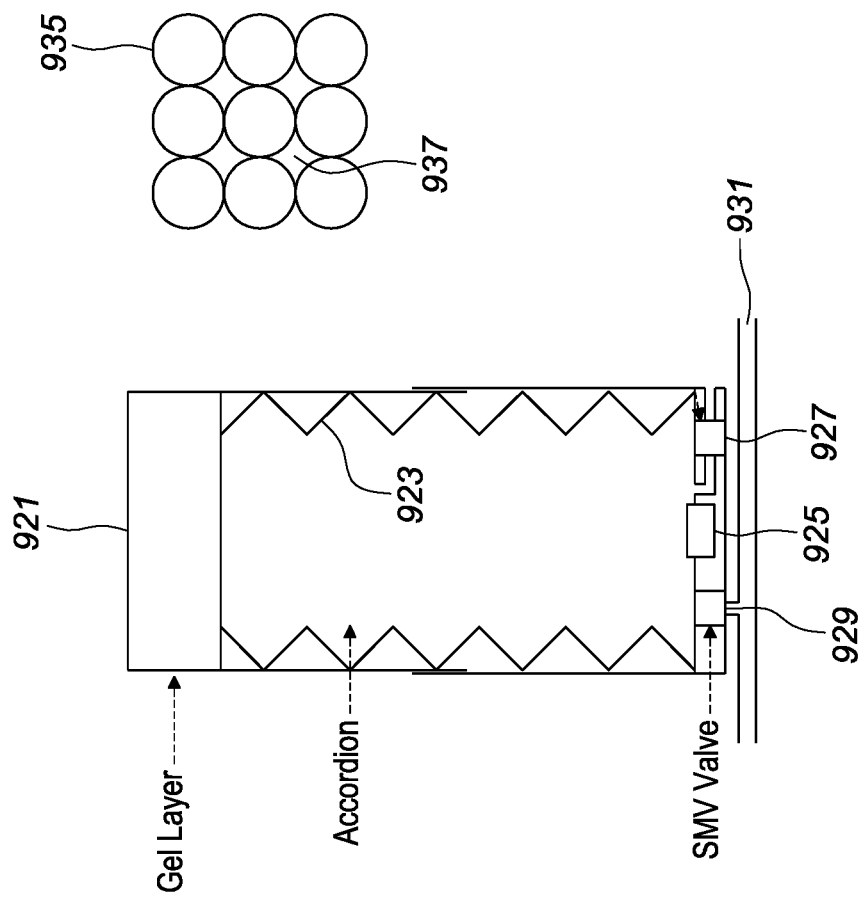
FIG. 9 shows information relating to an embodiment of a digital coil in accordance with aspects of the invention.
Figure 9:
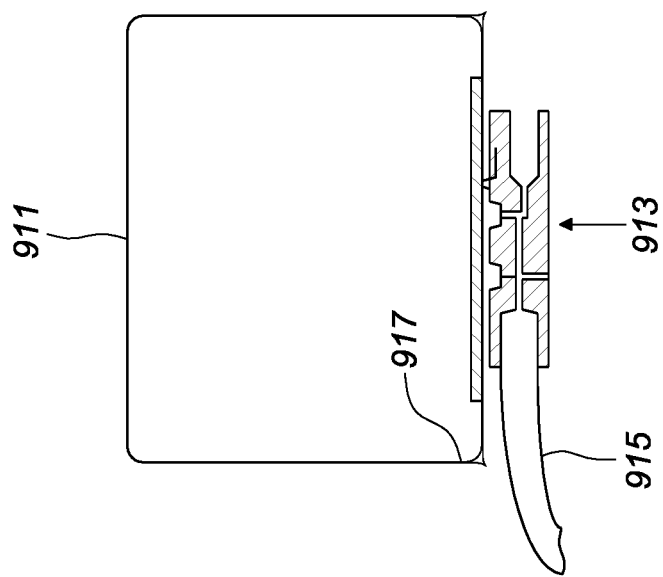

Alternative 1: Air Chamber: One embodiment includes a small air chamber with a predominantly solid state air control valve 913 connected to a shared pneumatic air line 915, as shown in FIG. 9. The embodiment of FIG. 9 may include some or all of: an air chamber provided by a bladder 911 (which may be sealed by way of a heat weld 917) or an accordion-like structure 923, a control valve, an electrical line to control valve and controller, which may be configured in a daisy-chain pneumatic configuration. Some embodiments may include integrated displacement and pressure sensors, a default state with no power or no connectivity, or alternative: with a combined foam 921 and air chamber. In some embodiments stepping motor valves 927, 929 (SMVs) may be used in regulating pressure, for example from a pressure supply line 931. A piezo crystal 925 may be used to monitor pressure. In some embodiments the digital coils 935 may be arranged in a two-dimensional array, with plenum 937 spaces between the coils.

Figure 10:
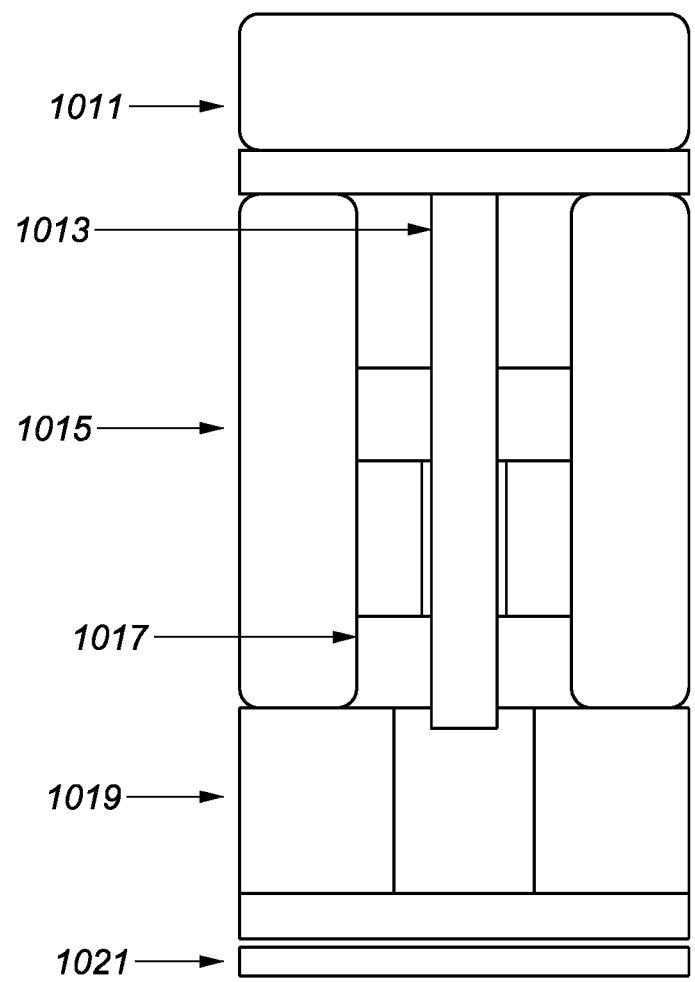
FIG. 10 shows further information relating to an embodiment of a digital coil in accordance with aspects of the invention.

A PZT piston design may be used in some embodiments (for example as shown in FIG. 10). Additional alternatives: one possible embodiment is a passive air chamber, possibly made of some form a plastic, rubber, or polyurethane, of various sizes and shapes. These passive air chambers can be connected by air tubes or lines to an electronically-controlled air valve or solenoid, which is controlled by a controller. In some embodiments a gel cushion 1011 is atop a piston 1013, operation of which expands or contracts an air donut 1015. Operation of the piston may be provided by a PZT "inchworm" 1017, which is atop a platform 1019. In some embodiments electronics 1021 for operating the coil is provided below the platform.

Each Digital Coil is electrically connected to a controller, which sends digital control signals to set firmness and/or displacement of individual digital coils. The controller can be local to each coil or a subset of coils, and those local controllers can also be connected to a regional controller that sends control signals to a large region or the entire bed surface. The control signals can be digital signals, which are converted by the local controllers into either analog or digital signals that can read by a mechanism inside the coil that sets pressure and/or displacement. For example, for an air-chamber based design described above, the solid state air control valve can receive analog control signals from the local controller. Alternatively, to minimize the total number of electrical wires in the coil array, the electrical connections between localized controllers and a global controller can be configured in a daisy-chain configuration, where each localized controller has an input and output that can be connected to an adjacent localized controller. Separately, electrical power can be delivered across to multiple digital coils by sharing a common power and ground line across multiple digital coils. Alternatively, one or more digital coils cam be connected by air tubes or lines to an electronically-controlled air valve or solenoid, which in turn is connected to an air pump and vent that can inflate or deflate the air chamber in a controlled manner. The electrical control signals to the air valve are generated by a controller, which generates digital control signals which can be converted into electrical control signals to each air valve.

Each Digital Coil may also or instead be connected to a pneumatic line, which can supply gas or liquid pressure to enable Digital Coil functionality. This hydraulic line can be shared across multiple digital coils to minimize tubing complexity, and hydraulic lines can also be connected to a common gas or liquid reserve tank to help maintain and regulate hydraulic pressure in the system.

In some embodiments Digital Coils Modules 415 may be used, with a module assembly of multiple digital coils in a Digital Coil Module, which may be housed in a module structural housing 211, 211a, 211b. Use of the Digital Coil Module to partitions digital coil array into smaller modules that enable the bed to be easily packed, shipped and assembled by the end-user. Also, the modules may allow for easier inventory management, be more cost-effective, and make repair and maintenance easier. The dimensions of a module can be defined to configure into multiple bed sizes using different numbers of modules in various orientations. The sizes may also be defined for easy handling and shipping for a single person to ship or receive, carry and assemble. These modules could be placed side-by-side into a cavity volume space designed at the core of the bed mattress, which is designed to accommodate multiple modules to fill the entire cavity. Each module can house uniform-sized coils, as shown in FIG. 2, or can house different sized coils to be placed in different regions of the bed to match required resolution of body parts and expected size of pressure points (see FIG. 2 and FIG. 3). FIG. 3 shows an example of two different sized digital coils being used for different bed regions, although other configurations and more than 2 sizes are also possible.

Figure 5:
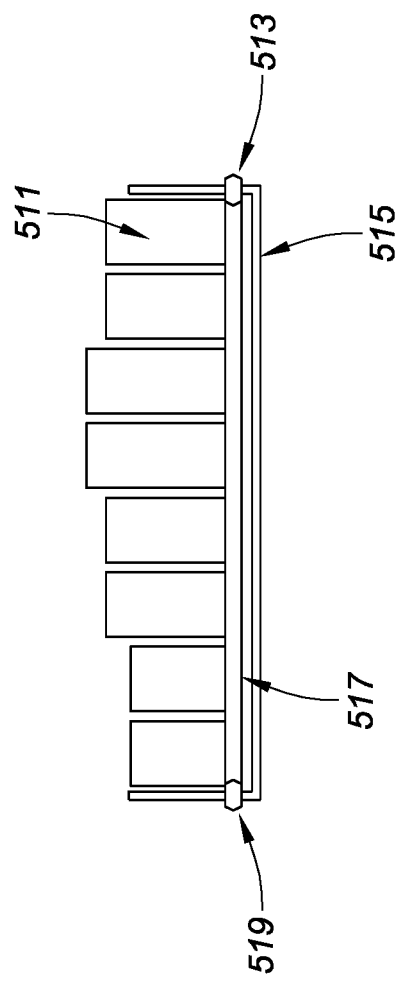
FIG. 5 shows a cross-sectional side view of an embodiment of a digital coil module in accordance with aspects of the invention.

As shown in FIG. 5, each module has a plurality of coils 511 and at least 2 connectors 513, 519, with a module structural housing 515. Each connector can support one or more of the following: electrical power and ground lines, digital electrical signal lines, and fluidic lines. Each connector can align and connect to an adjacent module to enable module-to-module connectivity or alternatively connect to the system controller and/or the central fluidic system. The interconnectivity between modules can provide in some embodiments connectivity from the system controller to all the modules in the system.

In some embodiments each digital coil area or multiple digital coil areas is coupled with either or both a pressure sensor and displacement sensor to generate real-time information about the topology and pressure map across the bed.

A pressure sensor measures pressure, which is the expression of the force required to stop a fluid from expanding, described as force per unit area. A pressure sensor acts as a transducer, generating a signal, typically electrical, as a function of the pressure imposed. Other names for pressure sensors include, but not limited to pressure transducers, pressure transmitters, pressure senders, pressure indicators, piezometers and manometers. There are many different types of pressure sensors; including but not limited to piezoresistive, capacitive, electromagnetic, piezoelectric, optical, potentiometric, resonant, thermal, and ionization. In some cases the pressure map may be binary indicating the presence of pressure above a threshold.

In some embodiments the pressures sensors are located anywhere along the air path. In some embodiments, an array of pressure sensors is integrated into the bed to generate information of a real-time pressure map across the bed surface, which can be used, for example by a controller such as a processor, to help determine information such as the presence of a person on the bed, body position, body state, high pressure points, and movement, which can then be used, together with other inputs and information from other sources, to determine appropriate dynamic changes to the sleep platform. In some embodiments, the pressure sensor can be connected where the air valve connects to the air tube that connect to the air chamber(s).

One embodiment includes at least one pressure sensor per digital coil area, which measures the local vertical pressure asserted from the bed surface in the local area of the individual digital coil. In some embodiments, the pressure sensor can be integrated into the digital coil itself. In some embodiments, if some type of liquid or gas (e.g. air) is used in the digital coil, the pressure sensor could measure the pressure of that liquid or gas, which would vary depending on how much weight is asserted on the bed surface directly above. In some embodiments, the pressure sensors could be located outside the digital coil assembly, either as part of the digital coil module assembly, or as part of different layer 411 above the digital coils, for example in modules 415, and possibly foam/gel layers 413, all of which may be supported by a structural base (see FIG. 4). An alternative embodiment would distribute one pressure sensor across multiple digital coils, for example in order to save costs or may be adequate to provide enough information about body position and state. The collective array of pressure sensors across the bed would be electrically, (and or data) coupled to a local controller or distributed multiple local controllers, which would process the signals from the sensors into digital information. In the latter case, the multiple local controllers could then be electrically (and or data) coupled to a global system controller that stores and processes the aggregated sensor information from the entire sensor array for the portion or entire bed.

A displacement sensor is a device that measures heights and/or distances. Displacement sensors can also be used together with other sensors, such as the pressure sensors, to help determine the various vertical heights, distances and relative distances in each or multiple digital coil areas. When collectively used as an array, these displacement sensors provide information of a real-time topology map of the bed surface, which can be used to help determine information such as body position, body state, body type and shape, body weight, and sleep stage, and can be used, together with other inputs and information from other sources, to determine appropriate dynamic changes that can be made to the sleep platform, as well as helping to classify the user into certain user groups that can identify what therapy profiles might work better for the user. Different displacement sensors types include but are not limited to laser sensors, LED sensors, ultrasonic sensors, contact sensors, and eddy current sensors.

A displacement sensor can be integrated into the digital coil assembly, for example as shown by sensors 215 in FIGS. 2 and 3, to measure the vertical height displacement of the individual digital coil. Alternatively, the displacement sensors may be integrated into the digital coil module assembly or the bed structure or other bed layers. An alternative embodiment would include one displacement sensor for multiple digital coils in order to save costs or may be adequate to provide enough information about body position and state.

The combination of information from the arrays of pressure and displacement sensors can be used, for example by a processor, to generate a detailed, real-time 3-D map of the body on the bed surface. This information can be used to analyze exact or relative, real-time body, spinal and neck alignment and position, body type and shape, and body state. It can also be used to determine any localized area on the bed surface that may need adjustments in reductions in firmness and support to alleviate high pressure points or increases in firmness and support to improve spinal alignment, neck and head positions, or uncomfortable or awkward body positions. For instance, one method implemented using at least one processor to improve sleep quality is 1) detect and determine the sleep state of the user, 2) determine the real-time body, spinal, neck positions and alignments and higher-pressure points from the information of these sensor arrays, 3) based on #1 and #2, determine what adjustments need to made, 3) make control changes to the digital coil array to adjust body position, alignments, and comfort. The timing and speed of these support changes may also vary and depend on 1) what sleep state the user is in, 2) the exact zone location (e.g. near head, legs, feet, or shoulders), 3) user preferences, or 4) user history (e.g. speed x has woken this user or other users, speed y has been used successful in the past and not woken up this user or similar other users) to ensure that the changes are not disruptive and uncomfortable.

In addition to dynamic surface control of support and firmness, some embodiments also integrate both continuous-periodic temperature sensing and dynamic temperature control apparatuses (heat/cooling) of individual zones across the sleeping area surface.

The array of temperature sensors provides information of a detailed, real-time temperature map of the bed surface. It is known that certain areas of the body are more sensitive to temperature. Instead of heating or cooling the entire bed or large regions of the bed, localized temperature control can be more effective in helping to regulate body temperature and comfort, especially if those temperature regulation are aligned to specific body part locations, which can move during sleep. Since the information from the pressure and/or displacement sensors can be used to determine position and location of the user's body parts at any given moment, this information can be used together with the temperature sensor information to enable dynamic control and regulation of the temperature of specific body locations, even with body movement or changing environment conditions. The precise control of heating or cooling of specific body parts (e.g. hands, feet, neck, torso) can be very effective, as well as energy efficient, in helping regulate overall body comfort and temperature.

There are variety of different materials and devices that can be used as a temperature sensor, such as thermistors, thermocouples, metal-based resistance temperature detectors, or a silicon-based band gap temperature sensor.

FIG. 3 includes an array of temperature sensors across the bed surface. Some embodiments include an array of temperature sensors distributed across the width and length of the bed to provide information of a detailed, real-time temperature map of the bed surface.

In one embodiment, there is at least one temperature sensor for every heat/cooling apparatus zone. Alternative embodiments could also have one temperature sensor for multiple temperature control apparatus zones, as well as multiple temperature sensors per single temperature control apparatus zone.

The locations and spatial resolutions of the temperature sensors can either be the same or different than those of other sensors, such as the pressure or displacement sensors.

The temperature sensors can also be distributed across the bed uniformly or non-uniformly. For instance, the upper body areas may need finer spatial resolution of temperature control vs. lower body areas, and there may be more temperature sensors, more densely distributed, in the upper body areas as a result.

Figure 4:
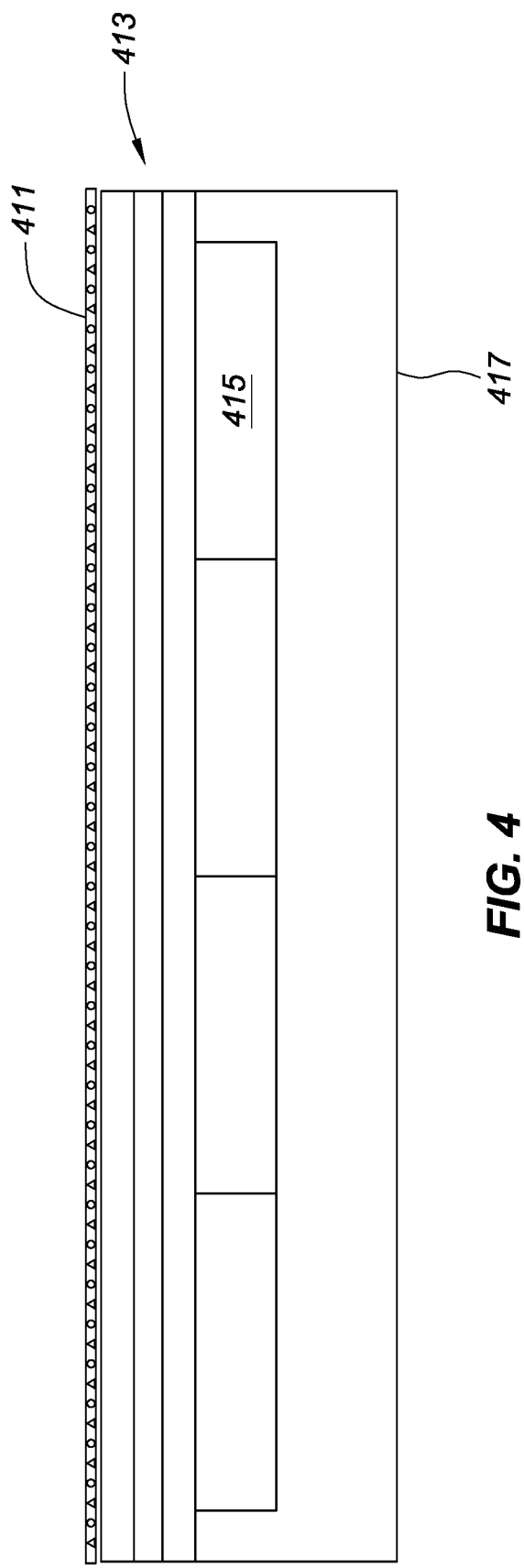
FIG. 4 shows a cross-sectional side view of an embodiment of a bed in accordance with aspects of the invention.

The temperature sensors can be located in any of the layers in the bed, with in some embodiments temperature sensors located in any one of the layers. FIG. 4 shows an integrated sensor layer 411 on the top layer of the bed, which could include temperature sensors. The temperature sensors could also be located in lower bed layers, such as foam or gel layers 413. The temperature sensors could also be integrated into the digital coil, either on the top surface of the digital coil or integrated into the digital coil in a chamber or space where gas or liquid exists. Temperature sensors can also be located to sense the ambient temperature.

Figure 6A:
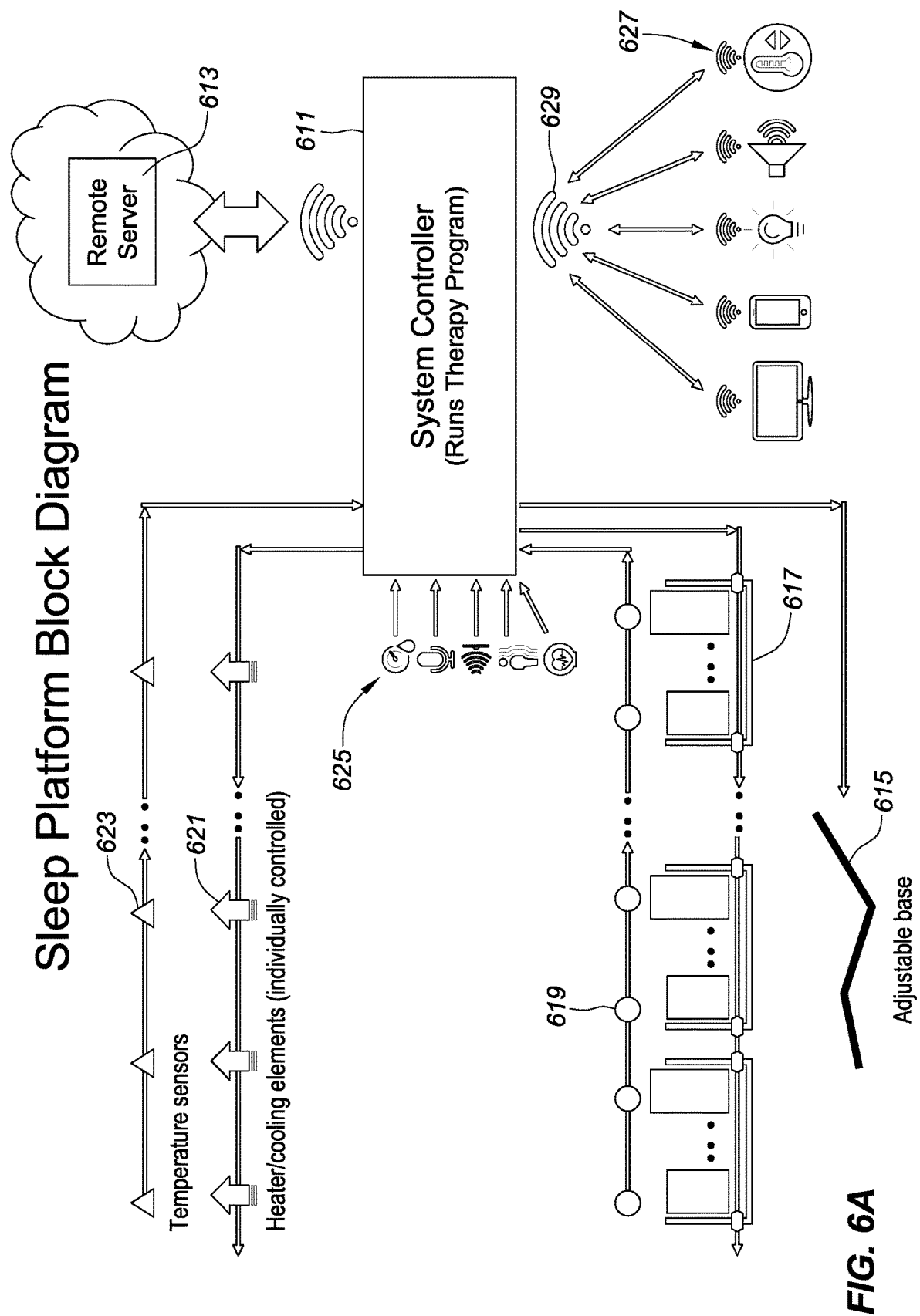
FIG. 6A shows a block diagram including aspects of an embodiment of a sleep platform in accordance with aspects of the invention.
Figure 6B:
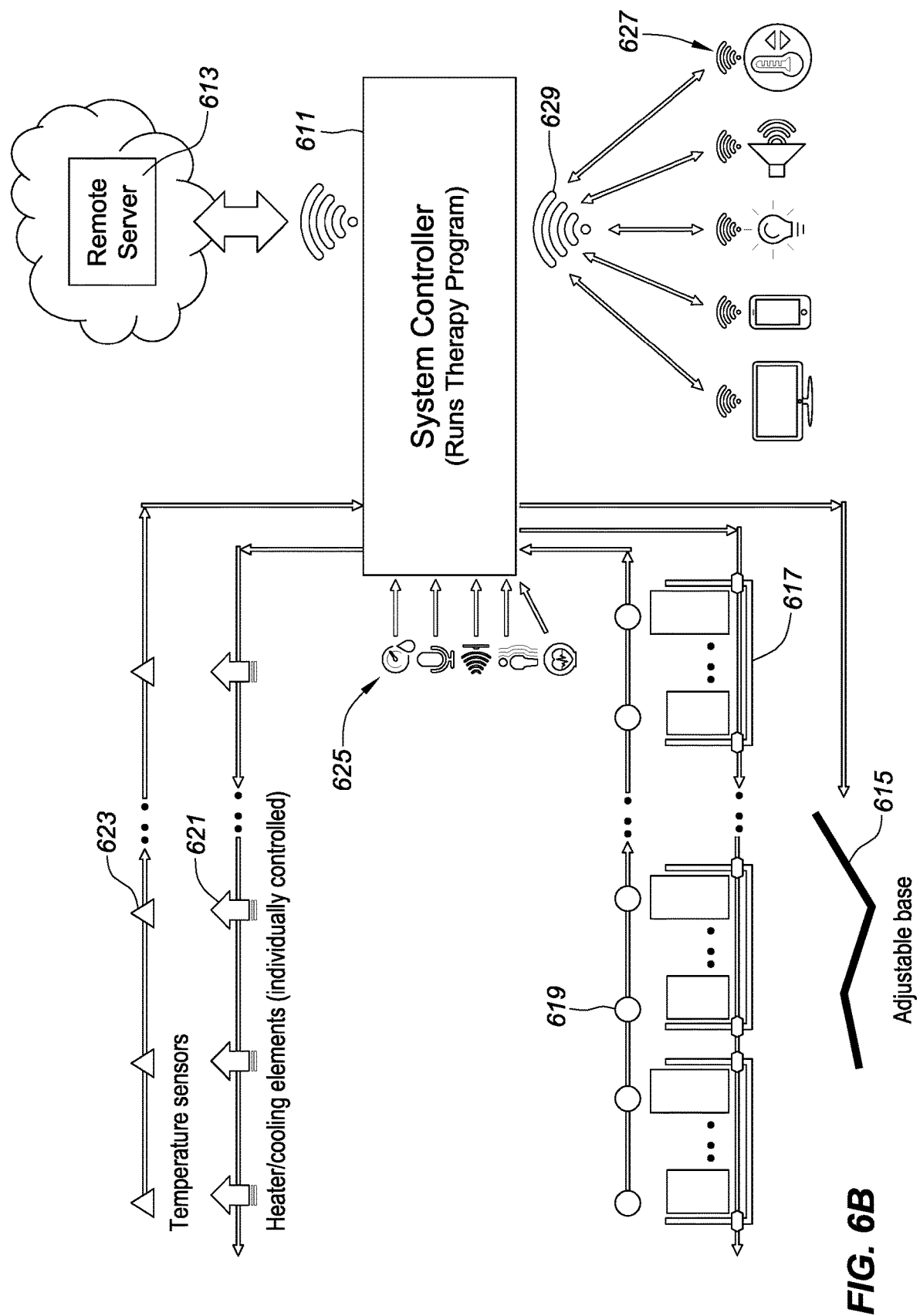
FIG. 6B shows a further block diagram including aspects of an embodiment of a sleep platform in accordance with aspects of the invention.

Multiple temperature sensors may be connected to either a local or system controller. As shown in FIGS. 6A and 6B, sensor information from pressure sensors 619 and/or temperature sensors 623 are collected and optionally processed by local controllers are sent to a system controller 611. The system controller can further store, organize and process that sensor data. This data can be processed and analyzed to determine the exact spatial temperature conditions of the sleep environment and then be used to determine control adjustments for coil modules 617 and for the temperature control apparatuses 621 in the sleep environment to improve sleeping conditions. The Z location temperature information can be used to calculate temperature gradients, further informing a temperature controller of appropriate actions. In some embodiments the system controller may also command position for an adjustable base 615.

Temperature control apparatuses (heating/cooling) in temperature control zones across the bed surface may be coupled with the temperature sensor array, some embodiments can also include one or more (an array) of temperature control apparatuses that can heat and/or cool various localized zones across the bed surface. In some embodiments, each control apparatus can be used to control a single temperature control zone. One or more temperature sensors may be associated with every temperature control apparatus zone. The temperature control apparatus can be embodied in various ways, including resistive electrical heating elements integrated into one of the bed layers, vented air channels for heating and/or cooling, or temperature control of the internal gases, air or liquids in the digital coil assembly. Temperature control zones can be oriented in a horizontally or vertically striped fashion or configured in a 2-D array configuration.

The temperature control apparatuses are connected to either a local controller or system controller, which set control signals that determine the heating or cooling setting of each apparatus. Each temperature of each zone can be separately controlled or multiple or all zones can be connected and regulated together to maintain a single target temperature across zones.

By utilizing the combination of pressure, displacement, and/or temperature sensor data, an example method performed by one or more processors for providing specific temperature control of targeted body zones in a sleeping environment may be as follows.

Step 1: Collect data from temperature sensor array, and collect data from pressure sensor array and/or displacement sensor array.

Step 2: Analyze pressure and/or displacement sensor data to determine real-time position of the user's body and identify exact locations of various body parts (e.g. head, neck, arms, torso, hips, legs, feet, etc.)

Step 3: Analyze temperature sensor array data to determine real time temperatures of various zones across the bed.

Step 4: Combine temperature zone data and body location data from Steps 2 and 3 to estimate the temperature of various body parts and zones of the user.

Step 5: Compare body part temperatures with hot and cold threshold temperature values to determine whether any specific body parts exceed threshold temperature settings.

Step 6: If temperature thresholds are exceeded in any body locations, determine new temperature apparatus control settings to either cool or heat the body location and send those updated control settings to the temperature control apparatus associated with the bed location next to the targeted body part location.

The platform can also include additional integrated sensors to determine the user's health vitals and statistics. The data from these sensors can be used to determine real-time vitals, which can include, but not limited to, motion, heart rate, heart beat signal signature and monitoring, respiration rate and signal, EKG, blood pressure, weight, sensor(s). This data can be used for several purposes including: to determine real-time sleep state and stages, to help track and monitor the sleep quality metrics and sleep history, to help track and monitor user health and body status, and to detect and identify potential health or sleep issues.

These health-related sensors can include, but are not limited to, motion sensors, such as accelerometers, or force/pressure sensors, such as piezoelectric-based sensors. These sensors can detect micro-movements of the body and translate those micro-movements into analog electrical signals that capture details of those movements. When adequately amplified and digitized, this information can be stored, processed and analyzed by a processor to perform techniques to extract physiological information, such as ballistocardiography (BCG), which is the technique of graphic representation and analysis of the movements of the body imparted by the ballistic forces (recoil and impact) associated with cardiac contraction and ejection of blood and with the deceleration of blood flow through the large blood vessels. These sensors can be used to monitor cardiac and respiratory activity. The data can also be used to help identify certain patterns or signatures in the activity that are associated with certain body state, sleep stages, activities, health conditions or issues, or sleep issues or conditions, cardiovascular issues, or other physiological state or conditions.

EKG (ECG) sensors may also be used. Electrocardiography (ECG or EKG*) is the process of recording the electrical activity of the heart over a period of time using electrodes placed on the skin. These electrodes detect the tiny electrical changes on the skin that arise from the heart muscle's electrophysiologic pattern of depolarizing during each heartbeat. An ECG can be used to measure the rate and rhythm of heartbeats, the size and position of the heart chambers, the presence of any damage to the heart's muscle cells or conduction system, the effects of cardiac drugs, and the function of implanted pacemakers. While traditional EKG uses electrodes attached to the skin, it is skin contact that is required and attachment is not required. ECG sensor materials can be integrated into the bed surface where there is often skin contact.

Photoplethysmography (PPG) senses the body's rate of blood flow using a light-based technology. PPG light emitters and sensors can be integrated into the bed surface.

Microphones positioned correctly near a sleep surface can sometimes pickup and detect a heartbeat and respiration. Microphones can also hear snoring, coughing, and other health related symptoms.

The data from these health sensors may also be used to detect or predict sleep or health issues. For instance, if certain combinations or patterns of health sensor data and history of the user, in combination with the other sensor data from the system, are compared to similar data from other user groups and there is high correlation with users with confirmed health issues or sleep disorders/issues, the user may be alerted and warned by the system. The system could also be designed to store key recommendations and helpful information for different user conditions, and that information can be automatically sent to the user in response to those issues being identified in the analysis. Also, based on the potential health or sleep issues identified, the exact sleep environment controls ("Therapy Profiles") may be modified to help address the issues identified. An audio microphone: used to track ambient and disruptive noise, detect snoring or breathing issues, or track breathing and movement, as indicated in FIG. 5. A light sensor may be used to track and detect the frequencies and intensity of ambient, daylight and artificial light, correlate with sleep activity and disruptions, align with circadian rhythms and schedules, use to target waking conditions or alarms, or use in conjunction of local room light controls (FIG. 5).

In some embodiments the bed platform is locally controlled by a local controller, for example as shown in FIGS. 6A and 6B. A local controller may be coupled to bed platform sensors, inputs, digital coils, temperature control mechanisms. A local controller system includes CPU processor, which can also be integrated into a system-on-chip (or SoC), memory, storage, network connectivity (wired and/or wireless). The local controller may be capable of running programs ("Therapy Programs") that monitor input signals and data, store and analyze those signals and data, match characteristic states, in real time determine and change dynamically control settings to the bed platform based on those real-time input signals and data, based on and updating historical data and trends. The local controller may be connected by network connection 629 to other network-connected devices 625, 627 in the house and bedroom to control extended bedroom and wider environment, for example lights, thermostat, humidifier, aroma diffuser, sound/audio devices.

The local controller can communicate over its network connection to remote server or servers 613 that receive data from the local controller and remotely run software programs that process the data from the local controller and can send data and updated control or program/software back to the local controller which can modify or change how the local controller works with the bed platform. The software and programs that run on both the local controller and remote server can execute methods that are in this document. Furthermore, an embodiment of the partitioning of how the software operates between the local controller and remote server is also discussed in the following section.

Analysis and Control Methods

In some embodiments, in order to make effective sleep environment changes in real-time to improve sleep quality, certain pertinent data can be collected and analyzed to determine specific user state and conditions, which can then be integrated with heuristic methods of environment improvements that translate into specific control instructions to make fine-resolution physical changes dynamically with the user's sleep environment in real-time. Some embodiments of this architecture supports the combination of pertinent data collection, methods of analysis and generation of control feedback instructions (e.g. improvement through iternative learning), and methods for multiuser and multi-instance analysis and learning, both locally and across larger groups. These methods, individually and collectively, can be used to dynamically adjust fine resolution physical controls of this sleep environment that uniquely enable improvements to sleep quality.

Methods to analyze conditions and context and dynamically adjust sleep conditions in real-time. Firstly, "real-time" for a sleeper can be defined as something that happens at an appropriate scale for a sleeper and need not be immediate and instantaneous. Over the course of a 7 hour sleep (420 minutes=25,200 seconds) it may sometimes be appropriate for a sleeper on a soft surface if the real time response to an event commences a few seconds after the event and takes place over a period of a few seconds.

Figure 7:
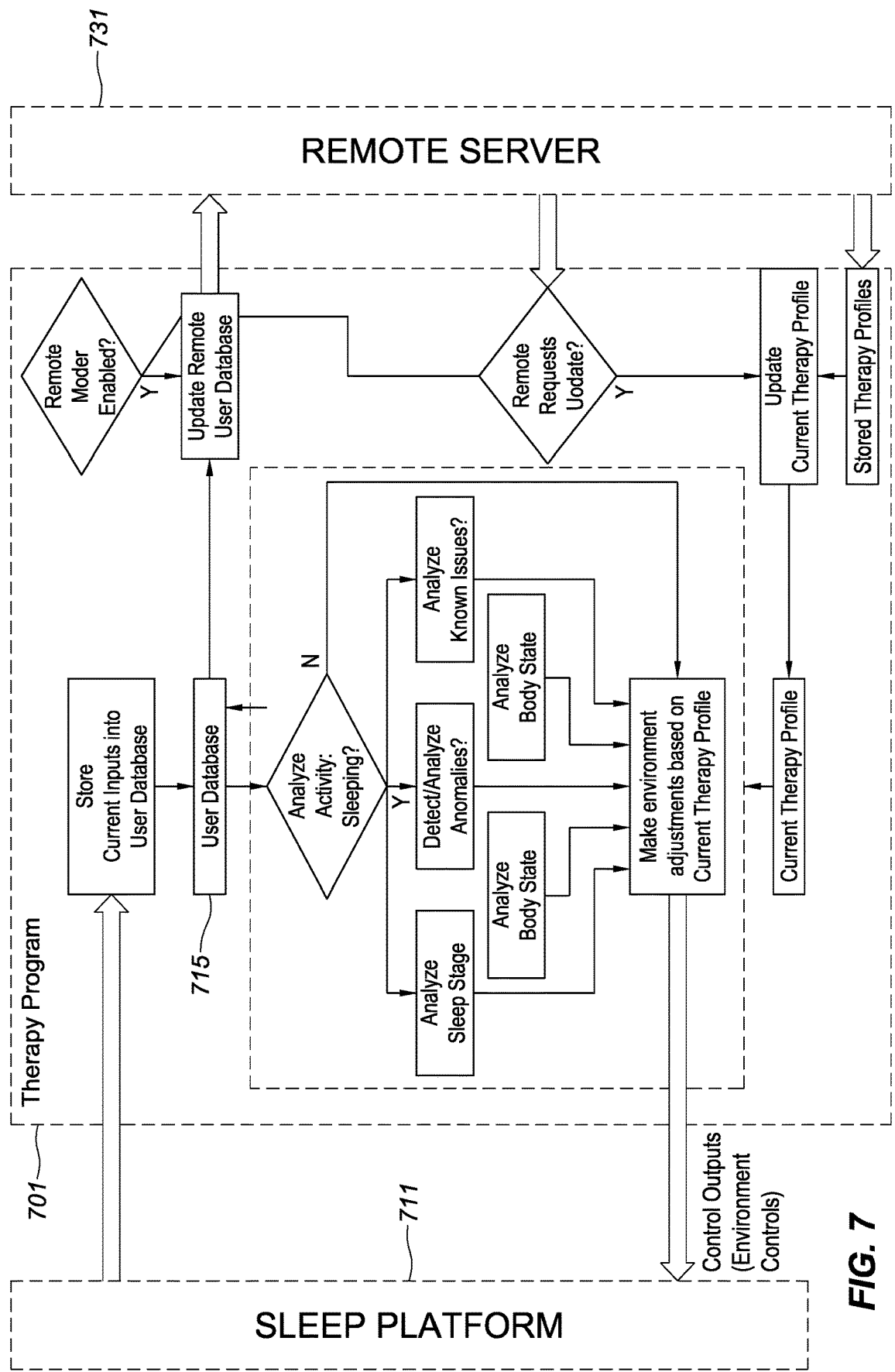
FIG. 7 shows a block diagram including a flow diagram of an embodiment of a therapy program in accordance with aspects of the invention.

A method for analyzing conditions and context and dynamically adjust sleep conditions in real-time is illustrated in FIG. 7, which diagrammatically illustrates operation of a controller 701 to control a sleep platform 711, with the controller in communication with a remote server 731. This method can be implemented in a software program, which, in one embodiment, can be called a Therapy Program, which can execute on the local controller shown in FIGS. 6A and 6B.

In some embodiments the program performs three basic functions: (1) input data collection, (2) determine user state and condition, and (3) determine settings (control outputs) for the sleep platform environment. These functions can be performed in real-time and allow for real-time analysis and dynamic control of the sleep environment based on changing conditions and user activity/state. For the latter two functions, the program may also relies on a collection of rules, threshold conditions and parameters, pre-determined data patterns, analysis guidelines, and control profiles, collectively called a Therapy Profile, that functionally determines the control settings of the sleep platform based on the input data. The Therapy Profile can be programmed and changed, either statically or dynamically. FIG. 7 shows the Therapy Program using a current Therapy Profile, which can be updated with a different Therapy Profile or additional Therapy Profiles either stored locally or sent remotely over the network from the remove server. More details of each of these three functions are described below:

Certain data is collected and analyzed to determine specific user state and conditions and effectiveness. This pertinent data may include data collected from the sensors integrated into the physical hardware platform along with timestamps in some embodiments, providing active collection of pertinent, real-time data (as discussed in the Physical Architecture section above). The data may also include personal user context information, including date of birth (for age), weight, height, sex, health condition, pre-existing health and sleep issues (such as pain points, injuries, insomnia, snoring, apnea), weight, weekly schedule and calendar events, diet, and emotional state. The data collected may also include user sleep preferences, such as sleep position preferences, sleep schedule, number of hours they ideally like to get or usually get, days they like to sleep in, sleep with partner or alone, and partner sleep preferences and requirements. The data collected may also include user feedback, which is provided by the user in response to the user's experiences or status.

The personal user context information can be collected directly from the user, for example, via a questionnaire or by the user allowing access to personal health records, or if the user opts in to allow the platform to access their personal smartphone databases such as calendar and activity tracker applications. The user feedback information could be accessed directly from the user on a regular basis; for instance, every morning upon wake up, users could answer a few questions on how they feel or how their sleep experience was that night. As shown in FIG. 7, these current data inputs can be collected and stored in a database 715 (User Database) along with data inputs from past history, which can then be analyzed (see below) and also shared with the remote server.

The program can use the data stored in the database to perform analysis to determine the user's state, context and conditions. Each target state, context or condition can be determined when the data is compared, matched, and/or correlated to pre-determined data patterns associated with each. If there is high correlation or high confidence of a match (as determined by preset thresholds), the user's state, context or condition can be classified and estimated and used to determine how the sleep platform environment may be adapted and adjusted to optimize sleep quality metrics. These computed user state, context and conditions can also be stored in the User Database, along with timestamps in some embodiments. These user state, context and conditions can include the following four examples, although other conditions and context can also be incorporated to the system:

The input sensors on the platform can detect motion and changes in pressure across the sleep surface, and log this over time, and if these data values have high correlation to patterns that represent sleep, the program can determine that the user is currently sleeping. Alternatively, if the data patterns have high correlation to other non-sleep activities (e.g. reading a book, watching TV, etc.), the program can also determine the user non-sleep activity state. Since the platform control settings depend greatly on the user's activity state and whether the user is asleep or not, this analysis is an important function.

The reference data patterns for different user activities and the correlation thresholds that are used to determine how well the user data patterns match the reference data patterns can be included as part of the Therapy Profile.

As discussed earlier, current clinical definitions consider four stages of sleep: REM (Rapid Eye Movement), and three non-REM sleep stages (NREM: N1, N2, and N3), where N3 is also called delta sleep or slow-wave sleep. Sleep quality and other functions of sleep such as feeling refreshed and memory consolidations are linked to the length and depth of sleep in REM and deep sleep stages (N3).

In various embodiments this system is able to estimate, in near real-time, the sleep stage of the user based on current and past input data from the platform (Current Inputs and Input Database). Sleep state can be estimated and determined with a combination of sensor data inputs, including but not limited to motion detection, heart rate, heart rhythm, heart electrophysiologic pattern or motion signature, temperature, body position, breathing rhythm and audio patterns. Sleep stage classification may always be an estimate, and it is well documented that two board-certified sleep scorers will assign different sleep states to the same subject. Sleep scoring is not always possible in real time, as some sleep states, according to the definitions of the states, can only be determined after the fact once the subsequent state has been determined. Real-time for sleep states for common medical use are in 30-second epochs.

The reference data patterns for different sleep phases and the correlation thresholds that are used to determine how well the user data patterns match the reference data patterns can be included as part of the Therapy Profile. Furthermore, the reference data pattern used for this collection of data for each sleep phase may be common across multiple users or also be unique to a given individual. This system platform is designed to identify, recognize and support both common and user-specific sleep stage recognition patterns.

Sleep quality and state can be highly dependent on the user's sleep position. Sleep position affects several factors including: uncomfortable pressure points, positioning of limbs, neck, head, back, including spine, neck and posture alignment, the positioning of head, neck and torso that determines how easily or difficult the user can breathe (e.g. snoring, apnea).

In typical clinical sleep stage recordings there are 4 primary sleep positions recorded: The body position (BPOS) of back (supine), left side, right side and front. However, within those 4 primary positions, there are many possible body and limb positions that can occur.

In various embodiments this system is able to determine, in real-time, the detailed body position of the user based on current and past input data from the platform (Current Inputs and Input Database). Sleep and body position can be estimated and determined with a combination of sensor data inputs, including but not limited to the pressure map of the pressure sensor array across the sleep surface, the temperature map of the temperature sensor array across the sleep surface, pre-calibrated information related to the exact user body dimensions, weight and shape, breathing rhythm, audio patterns, and heart data. This information can also be used and analyzed to estimate spine, neck and head alignment (or mis-alignment).

The reference data patterns for different sleep and body positions and the correlation thresholds that are used to determine how well the user data patterns match the reference data patterns can be included as part of the Therapy Profile. Furthermore, the reference data pattern used for this collection of data for each sleep position may be common across multiple users or also be unique to a given individual. In various embodiments this system platform may identify, recognize and support both common and user-specific sleep position data patterns.

Sleep quality can also highly depend on breathing effectively during sleep. Many people suffer from breathing issues, such as apnea, which involves the "suspension of external breathing". During apnea, there is no movement of the muscles of inhalation and the volume of the lungs initially remains unchanged. Also, many people suffer from snoring, which not only disrupts the individual's sleep quality but also others sleeping nearby.

In various embodiments this platform may help address breathing issues, so breathing status and breathing characteristic analysis is an important feature. In various embodiments this system is able to determine, in real-time, the exact breathing status of the user based on current and past input data from the platform (Current Inputs and Input Database). Breathing status and characteristics (for example dysfunction severity) can be estimated and determined with a combination of sensor data inputs, including but not limited to the audio signature of the breathing sounds and rhythm of the user, motion detection, heart rate, heart rhythm, heart electrophysiologic pattern or motion signature, temperature, and body position. The reference data patterns for breathing status and conditions and the correlation thresholds that are used to determine how well the user data patterns match the reference data patterns can be included as part of the Therapy Profile. Furthermore, the reference data pattern used for this collection of data for each breathing condition or severity may be common across multiple users or also be unique to a given individual. This system platform is designed to identify, recognize and support both common and user-specific breathing status and condition data patterns, which may be used to help modify or optimize the Therapy Program and Therapy Profile to adjust the sleep platform environment optimally to improve sleep quality.

In some embodiments another function of the Therapy Program is to use the collected data and determined user state and conditions from the first two functions to determine improved (possibly optimized) updated settings (or Control Outputs) for the sleep platform environment. The real-time adjustments to these settings helps enable the dynamic real-time improvements to sleep quality that this invention enables. In one embodiment, the Therapy Program performs this third function and this can be performed on the local controller (as shown in FIG. 7) or alternatively be performed on a remote server.

This third function can be described with the following equation:

$$o = TP(i\text{-}rt)$$

where $o=[o_1, o_2, o_3, \ldots o_m]$ represents the set of output setting values that control the sleep platform environment where $i\text{-}rt=[i_1, i_2, i_3, \ldots i_n]$ represents the set of real time inputs from the User Database and where TP represents the Therapy Profile, which is the function that maps the set of inputs, i, to a set of outputs, o.

Figure 8:
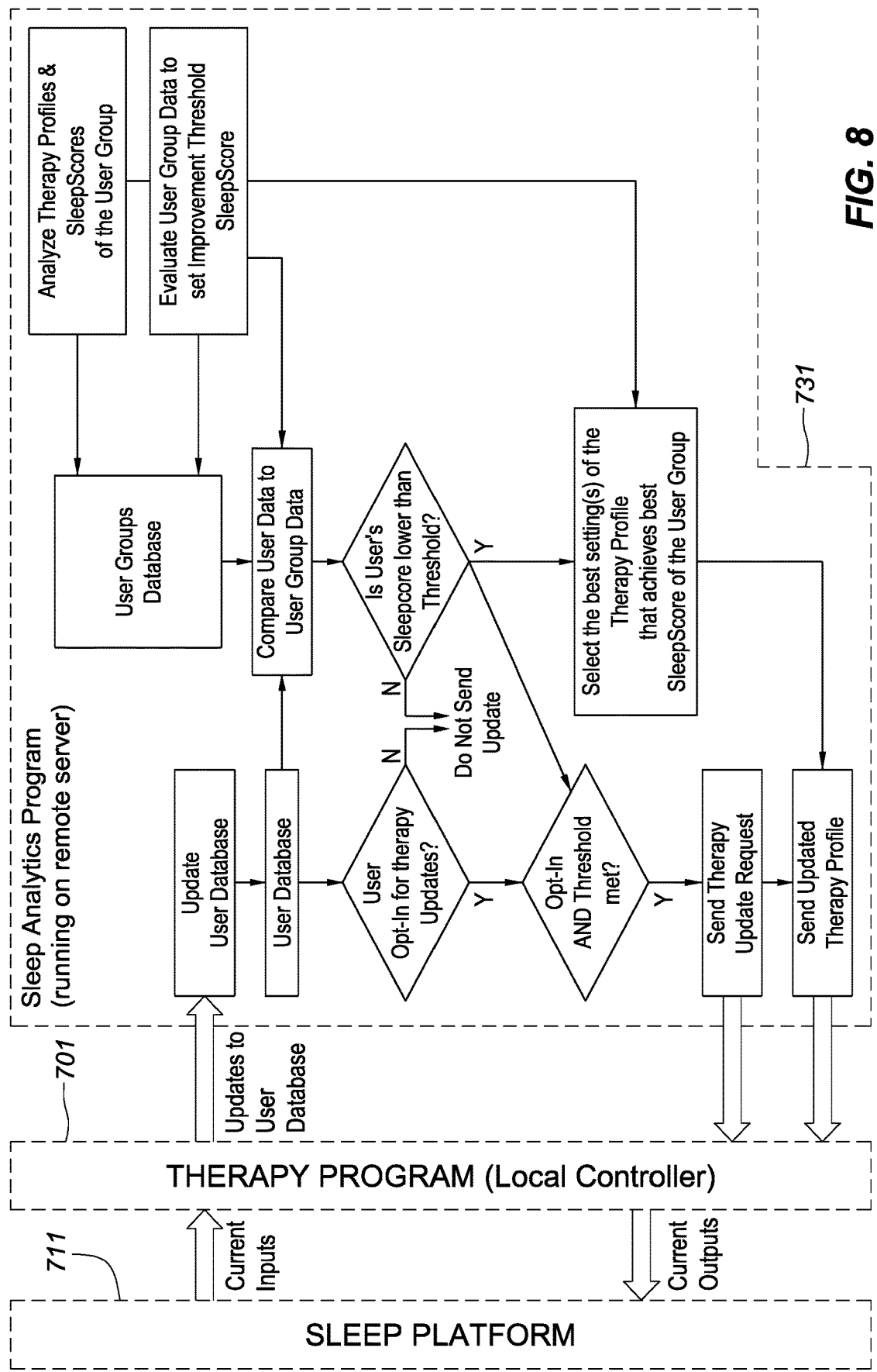
FIG. 8 shows a block diagram including a flow diagram of an embodiment of a sleep analytics program in accordance with aspects of the invention.

The Control Outputs shown in FIGS. 7 and 8 (and represented by the data vector, o, in the equation above) are the specific control signals and instructions that precisely set the specific configuration values and timing of the physical apparatuses of the sleep platform. Examples of this are the pressure value and displacement setting of each individual Digital Coil, and the transition timing on how quickly these settings change from the old to the new settings occur. Another example of this are the setting of either the heating or cooling elements, as well as the transition timing on how quickly these settings change from the old to the new settings occur. Further examples of this are extended environment output controls, such as lighting control, audio speaker volume and sounds (e.g. for alarm or music for going to sleep or waking up).

As discussed earlier, the Therapy Program relies on a Therapy Profile, which functionally determines how to determine the control output settings of the sleep platform based on the input and user data, and can incorporate different components, including a collection of rules, threshold conditions and parameters, pre-determined data patterns, weighting parameters, analysis guidelines, and control profiles.

There can be collection of multiple Therapy Profiles, each designed for different situations, and the Therapy Program can select and dynamically or statically change the Therapy Profile it uses, depending on different situations. For instance, some embodiments can allow for stage-specific Therapy Profiles, which adjusts different Therapy Profile settings depending on which sleep stage the user is in, or the part of the night (for example bed time, mid night, near wake up). Alternatively, some embodiments can enable position-specific Therapy Profiles, which adjusts different Therapy Profile settings depending on which sleep position the user is in. Once the exact sleep position is determined, the Therapy Program can determine and select which Therapy Profile and sleep platform environment output settings will be most effective is helping improve user sleep quality in real-time based on the current sleep position and sleep state. Furthermore, there can be dedicated Therapy Profiles for multiple combinations of user state or conditions, such as Therapy Profile that is optimized for a specific sleep stage, sleep position, breathing condition, body type, gender, and other specific user characteristics. Finally, the history of which Therapy Profile that is used along with timestamps can be recorded in the User Database, which can be used later to be analyzed for future improvements and optimizations.

In some embodiments TP=AF(i–h1, i–h2, i–h3, ... i–hn)
where TP is the therapy profile
where i–h=[$i_1, i_2, i_3, \ldots i_n$] represents the set of historical inputs from the User Database, for multiple people
and where AF represents some aggregation function (statistical pattern learning function) which maps the sequences of historical inputs from multiple people into a function (algorithm) that represent the historical data as a whole.

Therapy Profiles can be defined, adjusted and sorted using a software program that executes on a remote server that combines and analyzes the user data with larger user groups to determine the most effective settings, values and heuristic guidelines of different Therapy Profiles. FIG. 8 illustrates an example of this method of the software program, which in one embodiment is named the Sleep Analytics Program. In this program, Therapy Profiles can be defined and adjusted with the following steps: (1) Analyze and compare the user database and effectiveness of each component of a given user's Therapy Profile against those across different groups of targeted users. (2) Compare then identify the most effective setting for a specific component of a Therapy Profile across multi-users. (3) Adjust that user's Therapy Profile by using that identified, most effective setting. (4) Send the updated Therapy Profile to the user. (If the system supports an opt-in option for the user, the program can optionally send the update back to the user's platform depending on the user's opt-in setting.)

The effectiveness of any given Therapy Profile can be summarized as a value metric or collection of value metrics (in the example embodiment in FIG. 8, this metric is named SleepScore).

In one embodiment, the criteria of the Sleep Analytics Program can be set heuristically by medical or sleep experts who can evaluate the high-level analytics data, understand what it means, and determine criteria of the program, such as (1) How to categorize and partition various target user groups (2) Which components of each Therapy Profile should be analyzed and prioritized for different sleep conditions or situations (3) How to determine the weighting and criteria for the SleepScore value metric, which can combine some specific sensor data patterns with user feedback to make sure there is strong correlation with the value metric and actual sleep quality of the users.

As an alternative embodiment, a Therapy Profile can also include a set of expected or target SleepScore or set of expected or target sensor and/or system inputs. Once a Therapy Program has executed a given Therapy Profile, the resulting measured sensor and system inputs would be received and a Sleep Score can be computed by the Therapy Program. The Therapy Program can compare the Sleep Score to the expected/target Sleep Score of a given Therapy Profile. The Therapy Program can also compare the measured sensor and/or system inputs to the expected/target input values of a given Therapy Profile. If the Sleep Score and/or inputs match the expected/target values, the Therapy Profile is deemed effective and no further changes are made. However, if the expected values are not met, the Therapy Profile is changed to result in further improvements.

Examples of potential effective Therapy Profiles for a given user group may be for a user group that includes users that suffer from apnea and show significant sleep quality improvements when they sleep well on their side position vs. sleeping on their back (supine). The Sleep Analytics or Learning Program could select all the users that have apnea, analyze and select those whose breathing and snoring improved when sleeping on their side, evaluate the sleep platform output settings for all those who slept on their side to see which settings resulted in the longest, deepest sleep when sleeping on their side in the deepest sleep phases, the select the combination of the most effective settings to generate a combined Sleep Therapy Profile that works the best for this targeted user group, measure the effectiveness of those users who use this updated Therapy Profile to validate the benefits, and if positive, use this new Therapy Profile as the default setting for all those users in the target user group.

In one embodiment, the criteria of the Sleep Analytics Program can be automated. The Sleep Analytics Program could select all the users that have one sleep characteristic (for example predominantly side sleepers, or predominantly snoring) of similar sleepers. Analyze and select those nights whose sleep metrics are high and low (for example longest deepest sleep). Determine the sleep behavior and environmental states that are common for the higher sleep metrics and different for the lower metric sleepers. From this determine effective settings to generate a combined Sleep Therapy Profile that works the best for this targeted user group, measure the effectiveness of those users who use this updated Therapy Profile to validate the benefits, and if positive, use this new Therapy Profile as the default setting for all those users in the target user group.

Although the invention has been discussed with respect to various aspects and embodiments, it should be recognized that the invention comprises the novel and non-obvious claims supported by this disclosure.

What is claimed is:

1. A bed system, comprising:
    a sleep surface;
    a plurality of sensors for providing pressure information for a plurality of different zones of the sleep surface and sleep stage information of a user;
    a plurality of actuators to adjust pressures for the plurality of different zones of the sleep surface; and
    a first controller configured to receive the pressure information and to command the plurality of actuators to adjust the pressures to desired pressures based on the pressure information and a sleep therapy profile for the user on the sleep surface, the sleep therapy profile specifying the desired pressures;
    the first controller connected to a remote server over a network and configured to send the pressure information and sleep stage information of the user to the remote server; and
    the first controller configured to receive a new sleep therapy profile over the network from a remote server, the new profile, including new desired pressures, being determined by the remote server based on past information and sleep therapy profiles from the first controller and from a plurality of other controllers associated with other sleep surfaces.

2. The bed system of claim 1, wherein the sleep therapy profile includes a plurality of collections of desired pressures.

3. The bed system of claim 2, wherein the first controller is further configured to select a particular one of the plurality of collections of desired pressure based on a sleep position of the user, for use in commanding the plurality of actuators to adjust the pressures.

4. The bed system of claim 2, wherein the first controller is further configured to determine a sleep position of a user on the sleep surface based on the indications of pressure and at least one reference data pattern for the sleep position.

5. The bed system of claim 4, wherein the first controller is further configured to select a particular one of the plurality of collections of desired pressures based on the determined sleep position of the user, for use in commanding the plurality of actuators to adjust the pressures.

6. The bed system of claim 2, wherein the first controller is further configured to determine a sleep stage of a user on the sleep surface.

7. The bed system of claim 6, wherein the first controller is further configured to select a particular one of the plurality of desired pressures based on the determined sleep stage of the user, for use in commanding the plurality of actuators to adjust the pressures.

8. The bed system of claim 7, wherein the first controller is configured to determine the sleep stage of the user based on the indications of pressure.

9. The bed system of claim 7, further comprising additional sensors and wherein the first controller is configured to determine the sleep stage of the user based on indications from the additional sensors.

10. The bed system of claim 1, wherein the plurality of actuators comprise valves.

11. The bed system of claim 1, wherein the plurality of actuators comprise a plurality of arrays of actuators.

12. The bed system of claim 11, wherein actuators of a particular array of actuators are commonly controlled.

13. The bed system of claim 1, wherein the remote server determines the new sleep therapy profile based on information from other controllers associated with sleep surfaces of users sharing a common characteristic with the user.

14. The bed system of claim 13, wherein the common characteristic is personal user context information.

15. The bed system of claim 14, wherein the personal user context information includes age, weight, and height.

16. The bed system of claim 1, wherein the new sleep therapy profile is determined by selecting a profile that has resulted in improved sleep quality metric compared to the user's sleep quality metric of the existing sleep therapy profile.

17. The bed system of claim 16, wherein sleep stage information is used to determine the sleep quality metric.

18. A bed system, comprising:
- a sleep surface;
- a plurality of sensors for providing pressure information for a plurality of different zones of the sleep surface;
- a plurality of actuators to adjust pressures for the plurality of different zones of the sleep surface; and
- a first controller configured to receive the pressure information and to command the plurality of actuators to adjust the pressures to desired pressure targets based on the pressure information and a sleep therapy profile for the user on the sleep surface, the sleep therapy profile specifying the desired pressures; and
- the first controller connected to a remote server over a network which is configured to communicate with the user's personal smartphone and collect the user's feedback, the user's feedback used to determine the user's sleep quality score; and
- the first controller configured to receive a new sleep therapy profile over the network from a remote server, the new profile, including new desired pressure targets, being determined by the remote server based on the selection of a sleep therapy profile that provided an improved sleep quality score based on past information and sleep therapy profiles from the first controller and from a plurality of other controllers associated with other sleep surfaces.

* * * * *